(12) United States Patent
Hamidon et al.

(10) Patent No.: US 9,651,529 B2
(45) Date of Patent: May 16, 2017

(54) ARTIFICIAL OLFACTORY SYSTEM AND AN APPLICATION THEREOF

(71) Applicant: Universiti Putra Malaysia, Selangor (MY)

(72) Inventors: Mohd Nizar Hamidon, Selangor (MY); Nasser Lotfivandvahed, Selangor (MY)

(73) Assignee: Universiti Putra Malaysia, Serdang (MY)

( * ) Notice: Subject to any disclaimer, the term of this patent is extended or adjusted under 35 U.S.C. 154(b) by 261 days.

(21) Appl. No.: 14/284,617

(22) Filed: May 22, 2014

(65) Prior Publication Data

US 2015/0000373 A1 Jan. 1, 2015

(30) Foreign Application Priority Data

Jul. 1, 2013 (MY) .............................. 2013701159

(51) Int. Cl.
*G01N 33/00* (2006.01)
(52) U.S. Cl.
CPC ..... *G01N 33/0001* (2013.01); *G01N 33/0031* (2013.01); *G01N 33/0034* (2013.01)
(58) Field of Classification Search
CPC .................. G01N 33/0031; G01N 33/0034
See application file for complete search history.

(56) References Cited

U.S. PATENT DOCUMENTS

| 4,770,027 A | * | 9/1988 | Ehara | G01N 33/02 422/83 |
| 4,884,435 A | * | 12/1989 | Ehara | G01N 33/0031 422/83 |
| 4,890,478 A | * | 1/1990 | Claiborne | G01N 33/2841 73/19.11 |
| 5,051,240 A | * | 9/1991 | Nakai | G01N 33/0009 422/536 |
| 5,090,232 A | * | 2/1992 | Wakabayashi | G01N 33/0006 73/1.07 |

(Continued)

*Primary Examiner* — Lisa Caputo
*Assistant Examiner* — Punam Roy
(74) *Attorney, Agent, or Firm* — Suzannah K. Sundby, Esq.; Canady + Lortz LLP

(57) ABSTRACT

The present invention relates to an artificial olfactory system (100), comprising of an inlet (101); a gas chamber (110) having a detector means, connected to a data acquisition system (104); a heater (112) and a plurality of fans (115); a humidity absorber (111); an outlet (102); a vacuum pump (103); characterized by the detector means having a plurality of sensors (121) in each of a plurality of clusters (120), wherein the plurality of sensors (121) in each of the plurality of clusters (120) comprises identical sensors capable of responding to a particular gas or vapor. The present invention also relates to a method for detecting a gas or a vapor from the artificial olfactory system (100), comprising the step of exposing the gas or vapor to the plurality of sensors (121) to produce a plurality of output signals from the plurality of sensors (121); transferring the plurality of output signals to the data acquisition system (104); extracting median data from the plurality of output signals; applying a principal component analysis (PCA), neural network, and least square regression analysis on the median data from all of the plurality of clusters (120).

3 Claims, 4 Drawing Sheets

(56) References Cited

U.S. PATENT DOCUMENTS

| | | | | |
|---|---|---|---|---|
| 5,469,369 A * | 11/1995 | Rose-Pehrsson | G01N 29/022 | 340/632 |
| 5,654,497 A * | 8/1997 | Hoffheins | G01N 33/2829 | 702/27 |
| 5,807,701 A * | 9/1998 | Payne | C12Q 1/04 | 422/50 |
| 5,911,872 A * | 6/1999 | Lewis | G01N 33/0031 | 204/406 |
| 6,319,724 B1 * | 11/2001 | Lewis | A61B 5/00 | 422/68.1 |
| 6,537,802 B1 * | 3/2003 | Alocilja | C12Q 1/04 | 422/90 |
| 6,841,391 B2 * | 1/2005 | Lewis | A61B 5/00 | 422/82.01 |
| 7,103,481 B2 * | 9/2006 | Negri | G01N 33/0031 | 702/22 |
| 7,189,353 B2 * | 3/2007 | Lewis | G01N 27/126 | 422/50 |
| 7,460,958 B2 * | 12/2008 | Walsh | G01N 33/0034 | 702/24 |
| 2002/0092339 A1 * | 7/2002 | Lee | G01N 33/0011 | 73/23.2 |
| 2004/0016287 A1 * | 1/2004 | Fu | G01N 33/0031 | 73/23.34 |
| 2004/0147038 A1 * | 7/2004 | Lewis | A61B 5/00 | 436/149 |
| 2006/0155486 A1 * | 7/2006 | Walsh | G01N 33/0034 | 702/32 |
| 2010/0229658 A1 * | 9/2010 | Glezer | G01N 1/2273 | 73/863.81 |
| 2012/0024042 A1 * | 2/2012 | Vass | G01N 33/0031 | 73/23.34 |
| 2013/0061692 A1 * | 3/2013 | Muresan | G01N 33/0031 | 73/863 |
| 2013/0192332 A1 * | 8/2013 | Scheffler | G01N 35/00693 | 73/1.06 |
| 2016/0091470 A1 * | 3/2016 | Gafsou | G01N 33/0001 | 73/23.34 |

* cited by examiner

ARTIFICIAL OLFACTORY SYSTEM AND AN APPLICATION THEREOF

BACKGROUND OF THE INVENTION

Field of the Invention

This invention relates to an artificial olfactory system and a method for detecting gas or vapour using the system thereof, and more particularly to fault tolerant artificial olfactory system for detecting the concentration of the gas or vapour.

Description of Related Arts

Odours are complex mixtures of chemical species contain hundreds or thousands of constituent molecules. The biological olfactory system is a remarkable sensor which has some very important characteristics. There are many olfactory cells or adorant receptors. The characterization of a scent or odour is not through a specific receptor but through the combined response of a plurality of the receptors. In effect, the sensors respond broadly to a range or class of odors rather than to a specific one. This is the opposite to the ideal gas sensor, which responds to only one gas, and provides a unique output for a selective species.

For example, reports by Hayward et al. in 1977 disclosed the detection of metabolic volatile end products from E. coli and P. mirabilis using gas-liquid chromatography. In this work, the metabolic activity of bacteria on growth media led to the production of volatile chemicals that appeared in the head space of the growth vessel and were subsequently detected using a gas-liquid chromatography detector. Since different microbes display different metabolic pathways, it became feasible to distinguish between different species by recognizing the formation of specific volatile markers using the gas-liquid chromatography detection method. The work of Hayward et al. in 1977 showed this approach to be highly effective in the identification of E. coli and P. mirabilis. The cited art successfully applied the microbial odour analysis method to the rapid diagnosis of bacteria responsible for urinary tract infections using the chromatography detector. However, the use of chromatography detector has a high consumption cost.

There have been many attempts in the past to mimic the biological olfactory system. Most of them are based on existing gas-sensor technologies and have many drawbacks. Gas sensors made from tin dioxide are typical of current technology, and several commercial "electronic noses" have been based on tin dioxide arrays. Platinum pellistor-type elements, similar to tin dioxide sensors, require a high power consumption, which interferes with portability and low power operation.

U.S. Pat. No. 5,807,701 disclosed a method for the identification of microbes using arrays of sensors that respond to the different gases or vapours that are produced by different microbes grown in nutrient media. Since different microbial species display different metabolic products, a broadly responsive array is thought to provide a good detector in order to capture sufficient information to make subsequent predictions on which species are present more accurately. The sensors in the array interact with the different products causing multiple sensor signals that are subsequently collectively analysed by pattern recognition techniques using software. By using appropriate pattern recognition technique, it becomes possible to recognize sensor patterns produced by different microbes. However, the detection system should be improved with greater sensitivity and reliability.

Accordingly, it can be seen in the prior arts that there exists a need to develop an artificial olfactory system to meet the above critical needs and challenges.

REFERENCES

Hayward et al., Journal of Clinical Microbiology, September 1977.

SUMMARY OF INVENTION

It is an objective of the present invention to provide an artificial olfactory system for detecting aromas or odours.

It is also an objective of the present invention to provide an artificial olfactory system having a plurality of fault tolerant sensor array in each of a plurality of clusters.

It is yet another objective of the present invention to provide an artificial olfactory system which can detect the concentration of a detected gas or vapour.

Accordingly, these objectives may be achieved by following the teachings of the present invention. The present invention relates to an artificial olfactory system, comprising of an inlet; a gas chamber having a detector means, connected to a data acquisition system; a heater and a plurality of fans; a humidity absorber; an outlet; a vacuum pump; characterized by the detector means having a plurality of sensors in each of a plurality of clusters, wherein the plurality of sensors in each of the plurality of clusters comprises identical sensors capable of responding to a particular gas or vapour. The present invention also relates to a method for detecting a gas or a vapour from the artificial olfactory system, comprising the step of exposing the gas or vapour to the plurality of sensors to produce a plurality of output signals from the plurality of sensors; transferring the plurality of output signals to the data acquisition system; extracting median data from the plurality of output signals; applying a principal component analysis (PCA), neural network, and least square regression analysis on the median data from all of the plurality of clusters.

BRIEF DESCRIPTION OF THE DRAWINGS

The features of the invention will be more readily understood and appreciated from the following detailed description when read in conjunction with the accompanying drawings of the preferred embodiment of the present invention, in which.

DETAILED DESCRIPTION OF THE INVENTION

Figure 1:
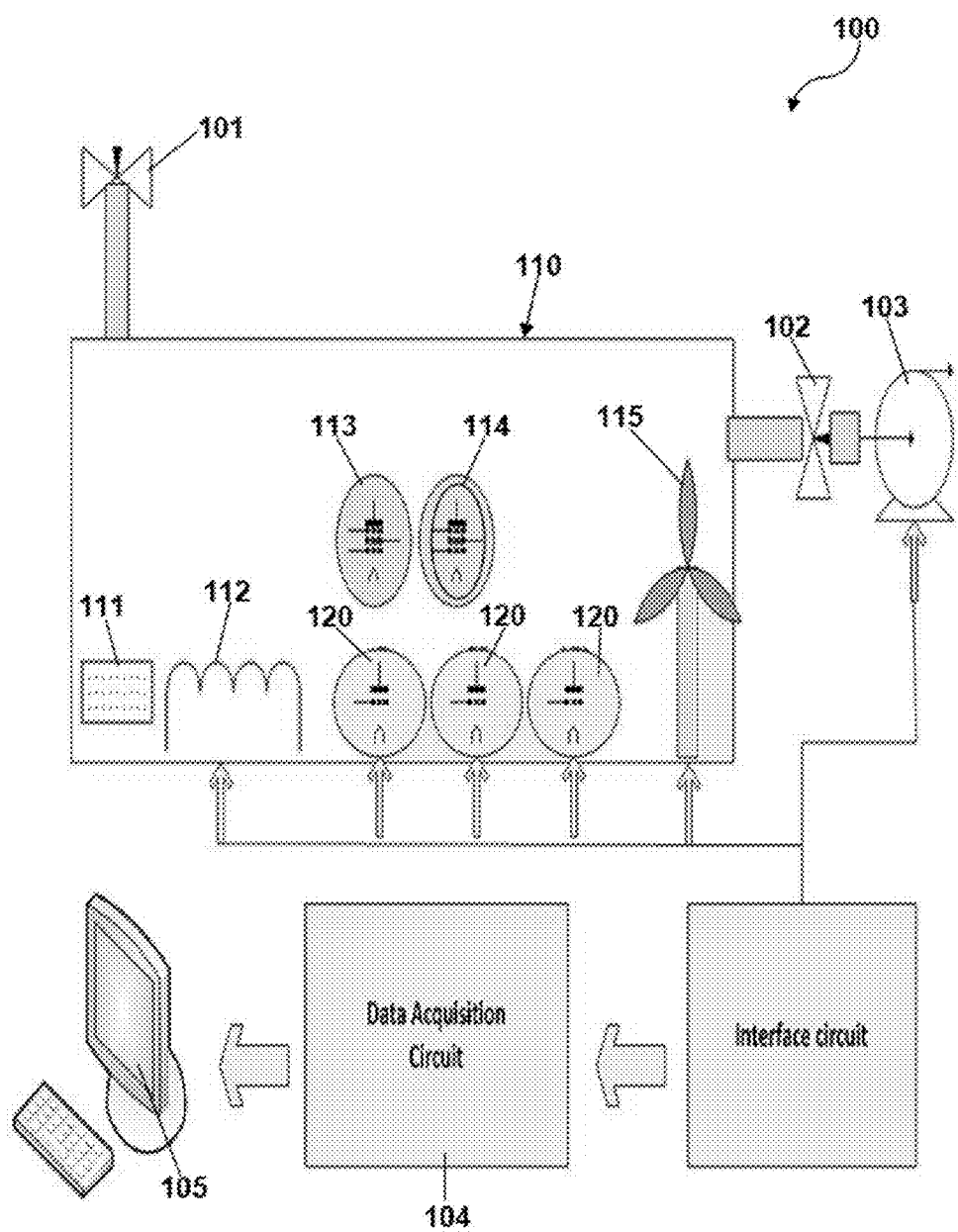
FIG. 1 is a schematic diagram of an artificial olfactory system.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting but merely as a basis for claims. It should be understood that the drawings and detailed description thereto are not intended to limit the invention to the particular form disclosed, but on the contrary, the invention is to cover all modification, equivalents and alternatives falling within the scope of the present invention as defined by the appended claims. As used throughout this application, the word "may" is used in a permissive sense (i.e., meaning having the potential to), rather than the mandatory sense (i.e., meaning must). Similarly, the words "include," "including," and "includes" mean including, but not limited to. Further, the words "a" or "an" mean "at least one" and the word "plurality" means one or more, unless otherwise mentioned. Where the abbreviations or technical terms are used, these indicate the commonly accepted meanings as known in the technical field. For ease of reference, common reference numerals will be used throughout the figures when referring to the same or similar features common to the figures. The present invention will now be described with reference to FIGS. 1-3b.

The present invention related to an artificial olfactory system (100), comprising of:
- an inlet (101);
- a gas chamber (110) having a detector means, connected to a data acquisition system (104);
- a heater (112) and a plurality of fans (115) for controlling the temperature in the gas chamber (110);
- a humidity absorber (111);
- an outlet (102);
- a vacuum pump (103) for eliminating remaining polluting gas or vapours;

characterized by:
- the detector means having a plurality of sensors (121) in each of a plurality of clusters (120), wherein the plurality of sensors (121) in each of the plurality of clusters (120) comprises identical sensors capable of responding to a particular gas or vapour.

In a preferred embodiment of the artificial olfactory system (100), the plurality of sensors (121) comprises a minimum of three sensors in each of the plurality of clusters (120).

In a preferred embodiment of the artificial olfactory system (100), the plurality of sensors (121) comprises gas sensors.

The present invention also provides a method for detecting a gas or a vapour from the artificial olfactory system (100), comprising the steps of:
- exposing the gas or vapour to the plurality of sensors (121) in the gas chamber (110); thereby producing a plurality of output signals from the plurality of sensors (121) in each of the plurality of clusters (120);
- transferring the plurality of output signals to the data acquisition system (104);
- extracting median data from the plurality of output signals from each of the plurality of clusters (120) by applying statistic median method;
- applying a principal component analysis (PCA) on the median data from all of the plurality of clusters (120) for gas or vapour identification and feature reduction;
- applying a neural network on the median data from all of the plurality of clusters (120) for evaluating the classification of the gas or vapour;
- applying a least square regression analysis on the median data from all of the plurality of clusters (120) to estimate the concentration of the gas or vapour.

In a preferred embodiment of the method for detecting a gas or a vapour from the artificial olfactory system (100), wherein the neural network is a multi-layer perceptron (MLP) classifier.

Below is an example of an artificial olfactory system (100) and its application from which the advantages of the present invention may be more readily understood. It is to be understood that the following example is for illustrative purpose only and should not be construed to limit the present invention in any way.

Examples

FIG. 1 is a schematic diagram of an artificial olfactory system (100). The artificial olfactory system (100) has a gas chamber (110) incorporated with an inlet (101) and an outlet (102). The inlet (101) of the gas chamber (110) allows a gas or a vapour to flow into the gas chamber (110), whereas the outlet (102) of the gas chamber (110) allows the gas or vapour to discharge from the gas chamber (110). A vacuum pump (103) is connected to the outlet (102) to eliminate remaining polluting gas or vapour which diffuses out from the gas chamber (110).

In a preferred embodiment, the gas chamber (110) is connected to a data acquisition system (104) which is manipulated by a computer (105). The data acquisition system (104) typically converts analog waveforms into digital values for processing. The data acquisition system (104), such as signal conditioning circuitry, converts sensor signals into a form that can be converted to digital values.

In a preferred embodiment, the gas chamber (110) comprises the detector means, the heater (112), the plurality of fans (115), the humidity sensor (113), the temperature sensor (114), and the humidity absorber (111). The heater (112) and the plurality of fans (115) are controlled by the temperature sensor (114) for controlling the temperature in the gas chamber (110).

In a preferred embodiment, the detector means has a plurality of sensors (121) in each of a plurality of clusters (120), wherein the plurality of sensors (121) in each of the plurality of clusters (120) comprises identical sensors capable of responding to the particular gas or vapour. The plurality of sensors (121) comprises a minimum of three sensors in each of the plurality of clusters (120). The plurality of sensors (121) is preferably comprises gas sensors.

Figure 3A:
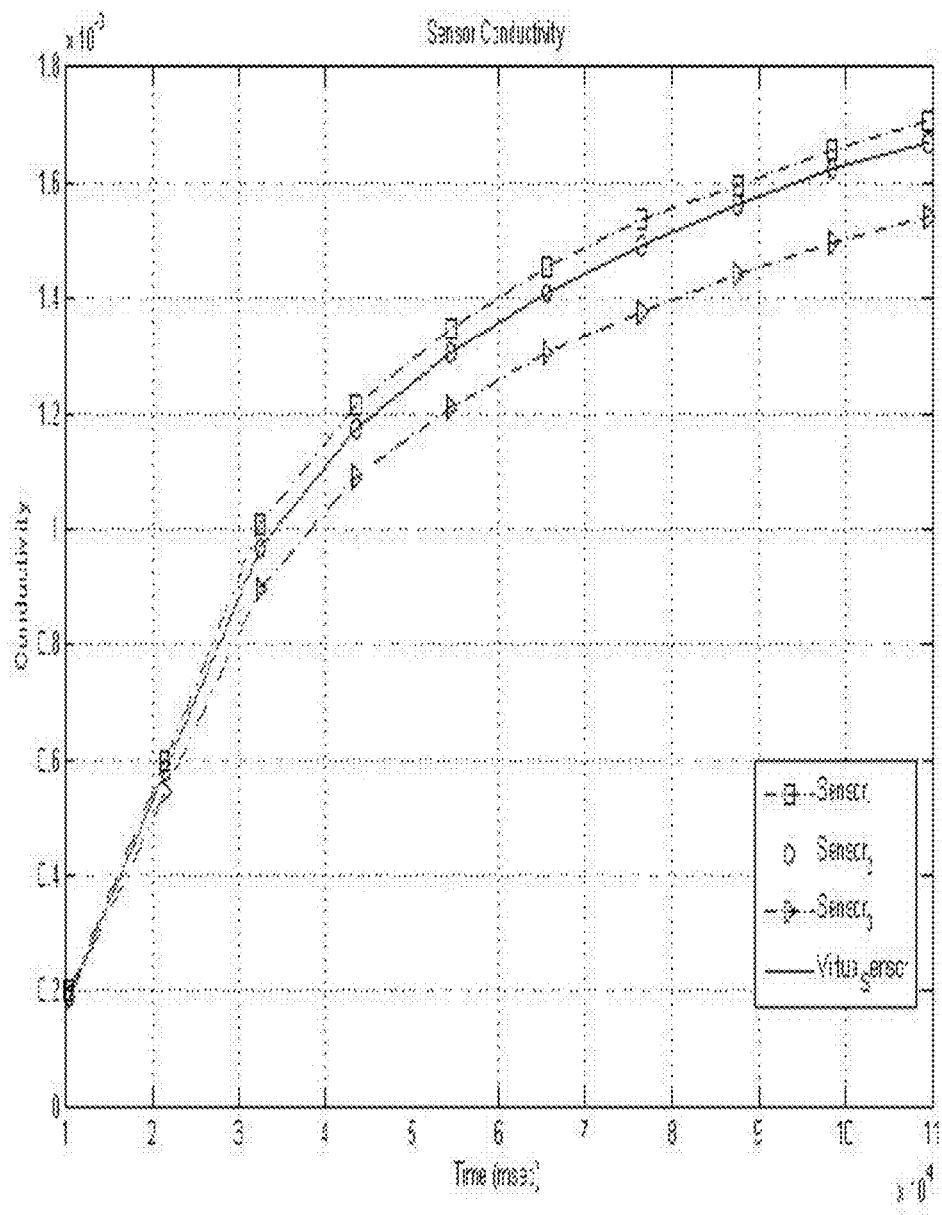
FIG. 3a is a diagram showing a sensor conductivity of each of a plurality of sensors.
Figure 3B:
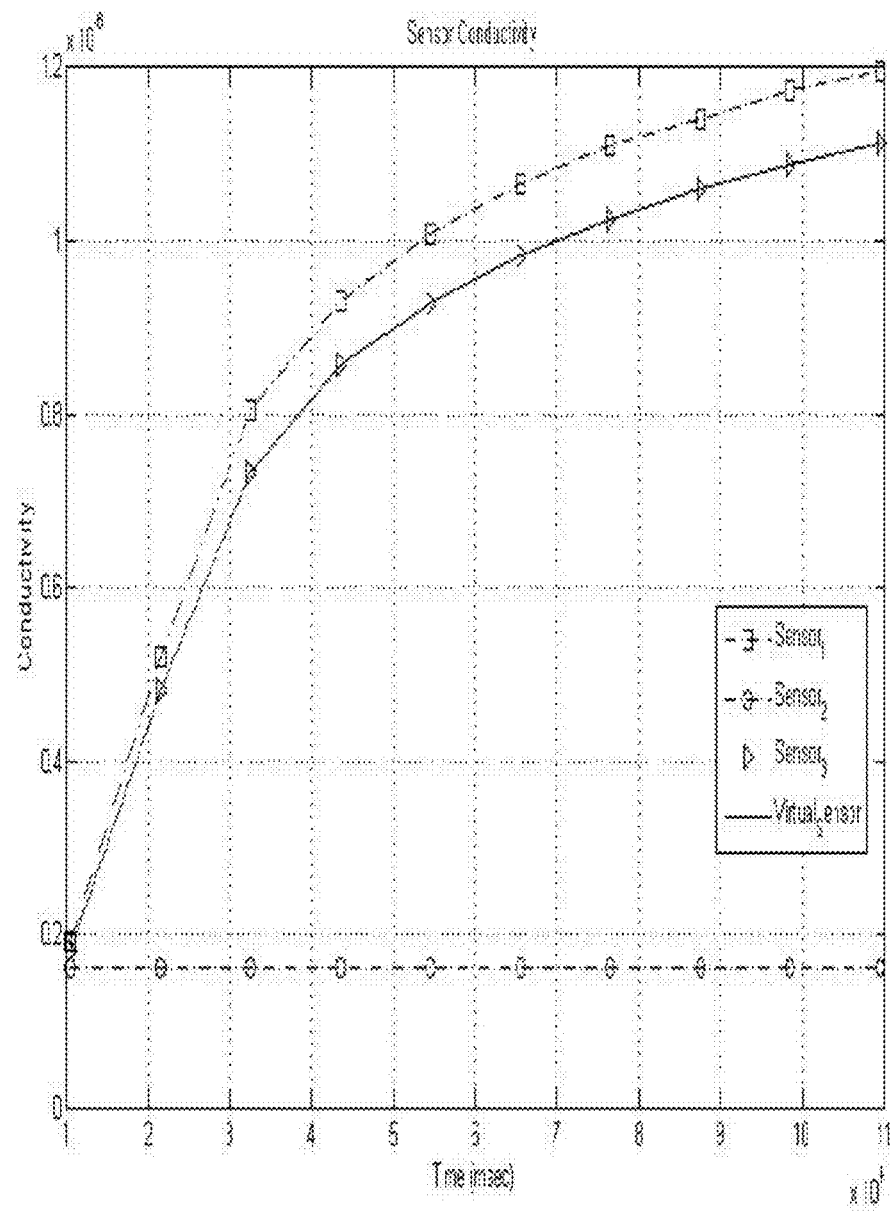
FIG. 3b is a diagram showing the sensor conductivity with one faulty sensor.

FIG. 3a is a diagram showing a sensor conductivity of each of a plurality of sensors. The artificial olfactory system (100) is said to be fault-tolerance if its performance is not affected by faults. This may be achieved by employing the plurality of sensors (121) in each of the plurality of clusters (120), preferably comprises at least three identical sensors which may contribute to the reliability of the artificial olfactory system (100). If one of the plurality of the sensors (121), for example sensor$_2$, is dysfunction as shown in FIG. 3b, therefore the rest of the plurality of sensors (121) in each of the plurality of clusters (120) will still give an accurate measurement and increase the reliability of this artificial olfactory system (100). The present invention detects the dysfunctional in the plurality of sensors (121) in each of the plurality of clusters (120) and uses the correct sensors to produce the output of the artificial olfactory system (100). The plurality of sensors (121) can be tested by reliability analysis.

Reliability Analysis

The plurality of sensors (121) preferably follows random failure and binomial process. The probability of the operation of the successful sensors can be calculated as following:

$$B(r:n) = \binom{n}{r} p^r (1-p)^{n-r}$$

wherein $$\binom{n}{r} = \frac{n!}{r!(n-r)!}$$

is the number of ways (arrangements) in which r successes (non-failures) can be obtained from n sensors;

wherein $p^r(1-p)^{n-r}$ is the probability of "r" successes and (n−r) failures for a single arrangement of successes and failures.

In an exemplary embodiment of the present invention, the reliability of one cluster of the plurality of the clusters (120) is calculated as following, wherein the one cluster of the plurality of the clusters (120) comprises three sensors. In the exemplary embodiment of the present invention, said one cluster of the plurality of clusters (120) has one faulty sensor and another two sensors in the good mode. The reliability of the one cluster of the plurality of clusters (120) is the sum of probabilities.

$$R_{cluster}(t) = B(3:3) + B(2:3);$$

$$R_{cluster}(t) = \binom{3}{3} R_{sensor}^3 (1 - R_{sensor})^{3-3} + \binom{3}{2} R_{sensor}^2 (1 - R_{sensor})^{3-2}$$

(all three sensors operating+2-out-of-3 sensors operating)

$$R_{cluster}(t) = = $$

$$\frac{3!}{3!(3-3)!} R_{sensor}^3 (1 - R_{sensor})^0 + \frac{3!}{2!(3-2)!} R_{sensor}^2 (1 - R_{sensor})^1$$

$$R_{cluster}(t) = 3R_{sensor}^2 - 2R_{sensor}^2$$

wherein $R_{sensor} = e^{-\lambda t}$
wherein $\lambda$ is the failure rate of the sensor.
Therefore, $$R_{cluster}(t) = 3e^{-2\lambda t} - 2e^{-3\lambda t}$$

Reliability of Sensor Array

To analyze this artificial olfactory system (100), the unreliability of cluster i is to be, $$Q_{cluster_i}(t) = 1 - R_{cluster_i}(t)$$

It is obvious that the sensor array will fail if and only if all its N clusters fail, or, $$Q_{sensor\ array}(t) = Q_{cluster_1}(t) \times Q_{cluster_2}(t) \times Q_{cluster_3}(t) \ldots \times Q_{cluster_n}(t) \ R_{sensor\ array}(t) = 1 - Q_{sensor\ array}(t) \ R_{sensor\ array}(t) = 1 - [(1 - R_{cluster_1}(t))(1 - R_{cluster_2}(t)) \ldots (1 - R_{cluster_n}(t))]$$

Therefore, the reliability of sensor array is as following:

$$R_{sensor\ Array}(t) = 1 - \pi_{i=1}^n (1 - R_{cluster_i}(t))$$

Method for Detecting a Gas or Vapour from the Artificial Olfactory System

In an exemplary embodiment of the present invention, the gas chamber (110) has a volume of 9 liters and is made of glass. The plurality of sensors (121) in each of the plurality of clusters (120) is kept in clean air in the gas chamber (110) for at least 10 minutes before conducting the gas or vapour detection method. In one exemplary embodiment of the present invention, the plurality of sensors (121) is preferably an alcohol gas sensor, wherein the alcohol is preferably selected from a group comprising of methanol, ethanol, propanol, or butanol. Since interfering environment parameters such as temperature and humidity affect reproducibility of the plurality of sensors (121), therefore the humidity and the temperature in the gas chamber (110) are monitored continuously and kept at constant level to eliminate interfering environmental factors and increase the reliability of the output measurement of the artificial olfactory system (100).

The voltage divider circuit with DC power is supplied to drive the plurality of sensors (121) in each of the plurality of clusters (120). The change of voltage in the constant resistor is used to evaluate the conductivity of the plurality of sensors (121).

The plurality of sensors (121) is exposed to the gas or vapour in the gas chamber (110), thereby producing a plurality of output signals from the plurality of sensors (121) in each of the plurality of clusters (120). The output signals are the measurement of voltage from each of the plurality of sensors (121). The plurality of output signals is transferred to the data acquisition system (104). The remaining polluting gases or vapours are diffused out from the gas chamber (110) by the vacuum pump (103) to decrease the recovery time and prevent long time gas exposition effects.

Figure 2:
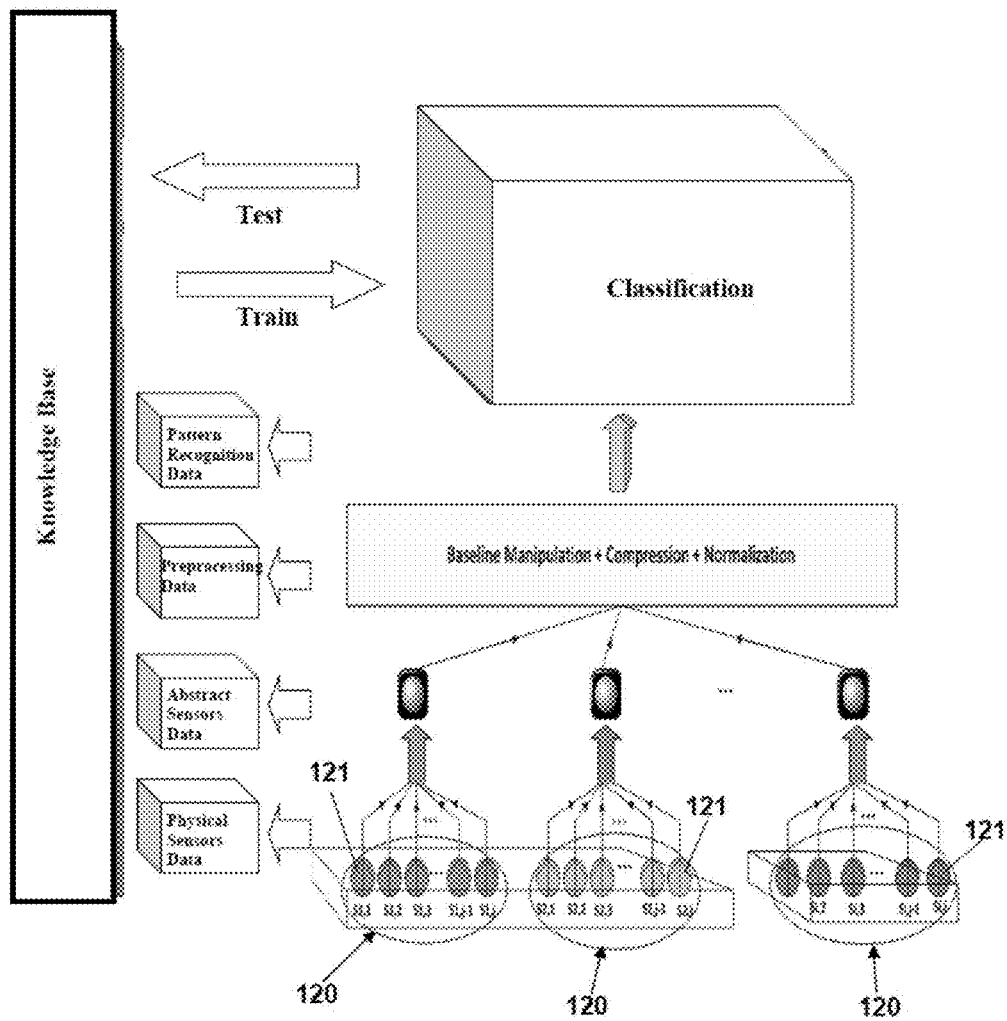
FIG. 2 is a diagram showing framework architecture of the artificial olfactory system.

FIG. 2 is a diagram showing framework architecture of the artificial olfactory system (100). The plurality of output signals from each of the plurality of clusters (120) is transferred to a virtual sensing system manipulated by the computer (105). The virtual sensing system uses information available from other measurements and process parameters to calculate an estimate of a median data. Therefore, the median data from the plurality of output signals from each of the plurality of clusters (120) is extracted by applying statistic median method in the virtual sensing system.

Signal preprocessing must be applied to modify the median data from all of the plurality of clusters (120) to minimize the impact of disturbances, which is generated by unequal responses of the plurality of sensors (121) and variability due to environmental disturbances. Preprocessing methods may include any of these three major categories: baseline manipulation, compression, and normalization. However, the preprocessing methods are basically common and obvious to a person who is skilled in the art.

In a preferred embodiment, the baseline manipulation method is preferably applied for reducing the effect of sensor drift. The sensor drift causes an unstable response over time with a slow and random variation of the baseline of the response generally. This baseline manipulation is preferably based on the calculation of variation of the median data produced follows the equation (1):

$$\Delta G(k) = G(k) - G(0) \quad (1)$$

wherein G(0) is the initial baseline median data from the virtual sensing system;

G(k) is the original median data from the virtual sensing system; and

ΔG(k) is the adjusted median data from the virtual sensing system.

The principal component analyses (PCA) is applied on the median data from all of the plurality of clusters (120) for gas or vapour identification and feature reduction. The feature reduction is to eliminate the curse of dimensionality in classification and improve efficiency, classification performance, and ease of interpretation and modeling. Extracted features by PCA are also projected to present the separability of different classes. A feed forward neural network is preferably used as multi-layer perceptron (MLP) classifier to evaluate the classification of the extracted features. The optimization algorithm is preferably the Levenberg-Marquardt (LM).

The performance of classifiers is customarily evaluated by a confusion matrix as illustrated in Table 1. The rows of the table are the actual class label of an instance, whereas the columns of the table are the predicted class label of an instance. Typically, the class label of a minority class set as positive, and that of a majority class set as negative.

TABLE 1

A confusion matrix for a two-class imbalanced problem

|  | Predicted Positive | Predicted Negative |
|---|---|---|
| Actual Positive | TP | FN |
| Actual Negative | FP | TN | wherein TP, FN, FP, and TN are True Positive, False Negative, False Positive, and True Negative, respectively.

From Table 1, the performance measures accuracy, precision, sensitivity (recall), on classification are defined by formulae in (2)-(4).

$$\text{Accuracy} = (TP+TN)/(TP+FN+FP+TN) \quad (2)$$

$$\text{Sensitivity} = TP/(TP+FN) \quad (3)$$

$$\text{Precision} = TP/(TP+FP) \quad (4)$$

A least square regression method is applied on the median data from all of the plurality of clusters (120) to estimate the concentration of the detected gas or vapour using the artificial olfactory system (100). The least square regression method may be common and obvious to a person having ordinary skill in the art to approximate the concentration of the gas or vapour.

Although the present invention has been described with reference to specific embodiments, also shown in the appended figures, it will be apparent for those skilled in the art that many variations and modifications can be done within the scope of the invention as described in the specification and defined in the following claims. Description of the reference numerals used in the accompanying drawings according to the present invention:

| Reference Numerals | Description |
|---|---|
| 100 | Artificial olfactory system |
| 101 | Inlet |
| 102 | Outlet |
| 103 | Vacuum pump |
| 104 | Data acquisition system |
| 105 | Computer |
| 110 | Gas chamber |
| 111 | Humidity absorber |
| 112 | Heater |
| 113 | Humidity sensor |
| 114 | Temperature sensor |
| 115 | A plurality of fans |
| 120 | A plurality of clusters |
| 121 | A plurality of sensors |

We claim:

1. A method for detecting a gas or a vapour, which comprises using an artificial olfactory system (100), comprising: an inlet (101); a gas chamber (110) having a detector means, connected to a data acquisition system (104); a heater (112) and a plurality of fans (115) for controlling the temperature in the gas chamber (110); a humidity absorber (111); an outlet (102); a vacuum pump (103) for eliminating remaining polluting gas or vapours; wherein the detector means comprises a plurality of clusters (120) and each cluster comprises a plurality of identical sensors (121) capable of responding to a particular gas or vapour, said method comprising the steps of:

exposing the gas or vapour to the plurality of sensors (121) in the gas chamber (110), thereby producing a plurality of output signals from the plurality of sensors (121) in each of the plurality of clusters (120);

transferring the plurality of output signals to the data acquisition system (104);

extracting median data from the plurality of output signals from each of the plurality of clusters (120) by applying statistic median method;

applying a principal component analysis (PCA) on the median data from all of the plurality of clusters (120) for gas or vapour identification and feature reduction;

applying a neural network on the median data from all of the plurality of clusters (120) for evaluating the classification of the gas or vapour;

applying a least square regression analysis on the median data from all of the plurality of clusters (120) to estimate the concentration of the gas or vapour.

2. The method for detecting a gas or a vapour according to claim 1, wherein the neural network is a multi-layer perceptron (MLP) classifier.

3. A method for detecting a gas or a vapour according to claim 1, wherein the minimum number of identical sensors (121) in each cluster is three.

* * * * *